United States Patent
Barr

[11] Patent Number: 5,279,559
[45] Date of Patent: Jan. 18, 1994

[54] REMOTE STEERING SYSTEM FOR MEDICAL CATHETER

[75] Inventor: Irwin R. Barr, Sparks, Md.

[73] Assignee: AAI Corporation, Cockeysville, Md.

[21] Appl. No.: 846,329

[22] Filed: Mar. 6, 1992

[51] Int. Cl.⁵ .......................................... A61M 37/00
[52] U.S. Cl. ...................................... 604/95; 604/281
[58] Field of Search .............. 604/95, 281, 264, 280–; 128/772, 657, 658

[56] References Cited

U.S. PATENT DOCUMENTS

| | | | |
|---|---|---|---|
| 3,470,876 | 10/1969 | Borchilon | 604/95 |
| 3,605,725 | 9/1971 | Bentou | 604/95 |
| 4,753,223 | 6/1988 | Bremer | 604/95 |
| 4,826,087 | 5/1989 | Chinery | 604/95 |
| 4,838,859 | 6/1989 | Strassman | 604/95 |
| 4,934,340 | 6/1990 | Ebling et al. | 604/95 |
| 5,078,684 | 1/1992 | Yasuda | 604/95 |
| 5,114,402 | 5/1992 | McCoy | 604/95 |
| 5,152,748 | 10/1992 | Chastagner | 604/95 |

Primary Examiner—C. Fred Rosenbaum
Assistant Examiner—Manuel Mendez
Attorney, Agent, or Firm—Venable, Baetjer, Howard & Civiletti

[57] ABSTRACT

Methods and apparatus are provided for remotely controlling the bending of an elongated member by implementing energy responsive control over a member that is configured from two plastic materials of differing coefficients of thermal expansion. The disclosed methods and apparatus are particularly applicable for use in applications such as surgical catheterization where control of the member from a position relatively remote from the member is desired.

57 Claims, 6 Drawing Sheets

REMOTE STEERING SYSTEM FOR MEDICAL CATHETER

BACKGROUND OF THE INVENTION

The present invention relates to a remote steering system that is primarily intended for use with surgical catheters. However, the invention may also be employed in connection with medical implants, switchgear and certain industrial pipeline equipment.

Surgical catheterization provides a desirable and readily implementable procedure for accomplishing various diagnostic and therapeutic objectives in a manner which is relatively expedient and free of trauma to the patient. In typical catheterization procedures, a blood vessel adjacent to the surface of the skin of a patient is punctured to provide entry of the catheter into the blood vessel lumen. Once entry of the blood vessel has been accomplished, the catheter can be advanced through the patient's vascular system, typically with the aid of various radiographic imaging techniques, to a desired internal organ or tissue site. Advancement of the catheter in this manner typically requires traversing a variety of angled and curved paths. Since many conventional catheters have generally cylindrical, flexible tubular structures, passage of the catheter along the desired angled or curved paths is accomplished by sliding the catheter over a guidewire.

Depending on the particular catheterization procedure and the path along which the catheter is to be advanced, the catheter guidewire may need to be changed on a number of occasions during the course of the procedure. Such guidewire changeover can be both time consuming and inherently risky, as vasculature of various dimensions must be traversed, possibly giving rise to incidents of vascular trauma and even rupture. Blood vessel rupture can radically transform the medical procedure from one of relatively routine diagnostic study to an emergency invasive surgical procedure, thus jeopardizing the health and even the life of the patient. Due to the foregoing difficulties and risks, surgical catheterization has evolved into a surgical specialty in its own right.

Previous efforts to produce remotely steered catheters have focussed on the use of shape memory metal alloys in order to provide desired curvilinear configurations for the distal ends of the catheters, so as to avoid altogether the requirement for guidewires. Examples of catheters employing shape memory metal alloys are disclosed in U.S. Pat. Nos. 4,994,727 and 4,919,133. As explained in the background portion of the latter patent, shape memory alloys are capable of transforming from a first configuration to a second configuration upon reaching a predetermined threshold temperature. This transformability apparently arises as a result of the crystalline structure that is imposed on the metal as a result of the particular metal annealing regimen that is employed. However, because shape memory alloys are generally "dormant" with respect to transformability until their respective transformation temperatures have been attained, catheters formed from such materials are generally unsuited for all but the most simple catheterization procedures. These catheters are generally transformable only into predetermined specific configurations rather than the broad range of configurations that are typically required to advance the catheter to remote internal sites incident to the performance of more sophisticated diagnostic and therapeutic procedures. For at least the foregoing reasons, catheters formed from shape memory alloys have not gained widespread acceptance for surgical catheterization on human patients.

SUMMARY OF THE INVENTION

In general, methods and apparatus are disclosed for implementing energy responsive control over the directional orientation or configuration of an object in response to thermal input. In one aspect of the invention, the device includes a generally cylindrical flexible member such as a catheter tube that is insertable into a conduit such as a blood vessel of a patient. The flexible member comprises a first layer that is formed from a non-metallic plastic material having a known coefficient of thermal expansion. A layer of a second non-metallic, plastic material having a coefficient of thermal expansion that is greater than that of the first layer is bonded in an appropriate manner to the first layer. A thermal energy supply system supplies thermal energy to the second layer from a position remote therefrom to effect expansion of the second layer and a change in angular orientation of the first layer. The thermal energy supply system can be in the form of a remote control device that is capable of delivering electrical or optical energy to the second layer for heating thereof.

Preferred materials for the first and second layers, which together form what may be referred to as a "bi-plastic", device, are selected from the families of PTFE fluorocarbons and silicone rubbers, respectively. However, other non-metallic materials having suitable physical and chemical characteristics for a given intended application, and which have sufficiently dissimilar coefficients of thermal expansion, can be used. A plurality of second layers can be positioned along the first layer at a common level thereof and can be arranged such that at least two of the material layers are independently controllable (i.e., non-slaved to one another) by the thermal energy supply means. Alternatively, the plurality of second layers can be arranged to form at least two discrete zones which are located at different longitudinal positions along the first layer. In such an arrangement, each of the zones can be independently controlled. Radio-opaque indicia can optionally be provided along at least a portion of the flexible member to facilitate visualization thereof during the course of radiographic imaging.

In an alternative aspect of the invention, an energy-responsive bi-plastic switch is provided that includes a first layer formed from a plastic material having a particular coefficient of thermal expansion and a second layer positioned along at least a portion of the first material layer. The second material layer is formed from a second material having a coefficient of thermal expansion at least two orders of magnitude greater than that of the first material and is responsive to thermal energy input to effect a change in directional orientation of the adjacent portion of the first layer. A source of energy can optionally be provided to supply energy to the second layer for conversion to thermal energy. Alternatively, the switch can be configured so as to derive thermal energy from the environment in which it is positioned to effect expansion of the second layer. Such switch configurational arrangements include, among others, configuration of the switch as an implantable for use in the body of a mammal for controlling mammalian body function in accordance with the magnitude of thermal energy received by the second layer of the switch. When the switch is to be used in conjunction with mammalian tissue, it is preferable to form at least one of the first and second layers from a material such as silicone rubber and a polymerized halogenated hydrocarbon, respectively, that is non-antigenic to mammalian tissue. In further arrangements of this aspect of the invention, the first layer of the switch can be configured as a generally cylindrical tubular member that defines a tubular lumen along at least a portion of its length, and the second layer can be positioned along an exterior surface of at least a portion of the tubular member.

The present invention further provides a method for effecting bending of a first member in response to thermal energy input to a second member positioned adjacent to the first member. The method comprises the steps of forming the first member from a non-metallic flexible material having a relatively low coefficient of thermal expansion, forming the second member from a non-metallic flexible material having a coefficient of thermal expansion at least two orders of magnitude greater than that of the first material, securing the second member along at least a portion of the first member, and supplying thermal energy to the second member to effect expansion thereof and bending of the first member in a predetermined direction generally away from the second member. At least one groove can be formed in the first member for receivably retaining therein at least a portion of the second member. The thermal energy can arise from optical or electrical energy and can be provided from an energy source to the second member through a suitably configured lead. Although a variety of optical energy wavelengths can be employed, energy having a wavelength from about 750 nm to about 900 nm is preferred for many high coefficient of thermal expansion materials. A tunable GaAlAs (Gallium Aluminum Arsenide) laser is the preferred source of optical energy.

BRIEF DESCRIPTION OF THE DRAWINGS

Various other features and advantages of the present invention will become apparent from a reading of the following detailed description in conjunction with the accompanying drawings, in which.

DETAILED DESCRIPTION OF THE PREFERRED EMBODIMENTS

Figures 1, 4A, 4B:
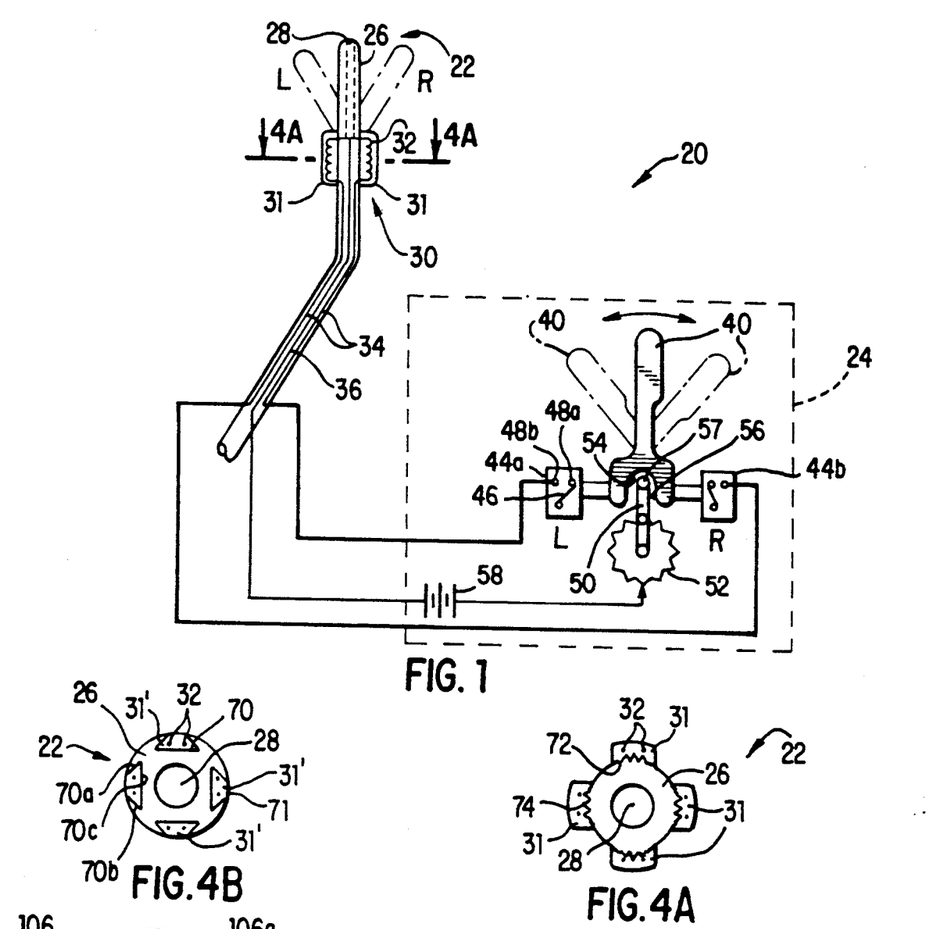
FIG. 1 is a schematic side view of a remotely-controllable catheter device in accordance with the present invention.
FIG. 4A is a cross-sectional view of the distal end of the catheter device taken along line 4A—4A of FIG. 1, illustrating four directional reorienting devices.
FIG. 4B is an alternative cross-sectional view of the distal end of the catheter device.

With reference to the drawings, wherein like reference characters represent like components throughout the various views, and with particular reference to FIG. 1, there is depicted a bi-plastic thermal energy responsive device in the form of a remotely-controllable catheter device 20 that is particularly advantageous for use in surgical catheterization procedures. It is to be appreciated, however, that the thermal energy responsive device of the present invention has a wide variety of uses and can be configured in a broad range of forms other than remotely controllable catheter devices to attain a desired utilization objective. Such alternative uses can include, for example, exploration of the interior surfaces of conduits such as machinery pipelines and internal components that would otherwise not be possible in the absence of disassembly.

The catheter device 20 generally comprises an elongated cylindrical catheter 22 and a remote catheter control unit 24 designated within the confines of the box depicted in phantom. The catheter 22 comprises a catheter tube 26 that is dimensioned to be received within the lumina of major blood vessels such as the saphenous vein. Preferably, the catheter tube 26 is formed from a non-metallic, plastic, chemically and hermetically stable material such as any one of the family of polymerized halogenated hydrocarbons which include the polytetrafluoroethylenes (PTFE) compounds. As used herein, the term "plastic" refers to the family of synthetic or natural organic, non-metallic materials which are capable of being shaped when soft and then hardened. The family of PTFE compounds are also noteworthy for their relatively high degree of thermal stability, remaining chemically and physically stable when exposed to temperatures in excess of 400° F. (222° C.).

The catheter tube 26 defines a tubular lumen 28 through which material such as a suitable radio-opaque dye or other fluid material or suitably-dimensioned instrument can be passed. A catheter tube directional reorienting assembly 30 is provided on the catheter tube 26 and includes four reorienting devices 31 (only two of which are shown in FIG. 1). The reorienting devices 31 are preferably positioned diametrically opposite each other as shown in FIG. 4A. Depending on the degree of directional control of the catheter tube 26 desired, more or less reorienting devices 31 may be employed per assembly 30, and more than one assembly 30 may be positioned along the length of the tube 26.

Figure 2:
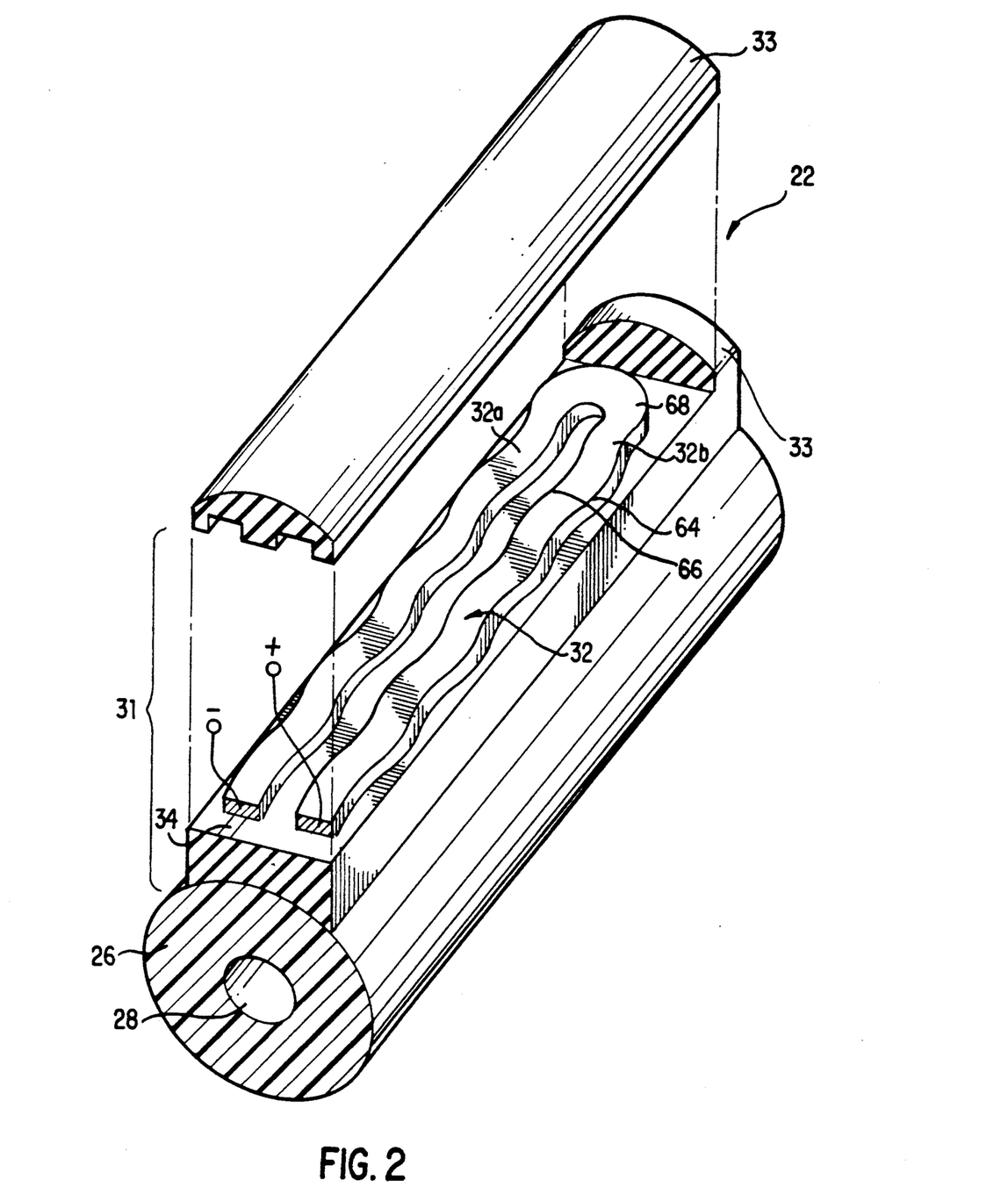
FIG. 2 is an enlarged partially exploded view of the distal end of the catheter device depicted in FIG. 1, illustrating a directional reorienting device.

With reference to FIG. 2, one of the reorienting devices 31 is shown mounted to a portion of the catheter tube 26. The reorienting device 31 comprises a layer 33 of suitable plastic material such as silicone rubber which exhibits a comparatively greater degree of response to thermal energy input than does the material comprising the tube 26. Material selection for the tube 26 and respective layers 33 can vary in accordance with such factors as the chemical and thermal characteristic of the intended use environment, material compatibility, and the like. For example, use in the human body imposes the requirement that the device not contain materials that are antigenic to human tissue and fluids. Furthermore, enhanced device response can be obtained through the use of materials having more widely disparate coefficients of thermal expansion than the family of PTFE compounds and silicone rubber.

Material heating apparatus such as a resistance heater wire 32 is embedded in the plastic layer 33 of the reorienting device 31 in order to provide thermal energy input in the form of resistance heat. The resistance heater wires 32 are preferably formed from a relatively high resistance metal such as an 80:20 nickel-copper alloy and are supplied with electrical energy via electrical conductors 34 which are preferably secured to or embedded in the catheter tube 26. The opposite ends of the resistance heater wires 32 are connected to a suitable ground wire 36, which is also secured to the tube 26 in a conventional manner. The respective conductor and ground wires 34 and 36 pass from the catheter tube 26 to the remote control unit 24.

The remote control unit 24 includes a suitable control input device such as a joystick controller 40 that is displaceable in the manner indicated in phantom in FIG. 1. Displacement of the joystick 40 in either of the positions indicated in phantom effects engagement of a corresponding one of the respective toggle switch actuators 42a and 42b. Each of the actuators is respectively coupled to a conventional toggle switch 44a, 44b. The toggle switches 44a and 44b are of conventional design and include a toggle arm 46 that is selectively displaceable between contact poles 48a and 48b. As can be appreciated from reference to the drawing, contact pole 48a represents a switch "open" position, whereas pole 48b represents a switch "closed" position. Each of the respective toggle arms 46 is normally biased so as to orient the switch in an "open" position. Displacement of the joystick 40 to the left or to the right effects closing of the corresponding switch 44a, 44b by way of the associated switch actuator to provide for displacement of the distal end of the catheter tube 26 in a corresponding direction in the manner described below.

A pivotably-mounted contact arm 50 coupled to a variable resistor or potentiometer 52 is received within a recess 54 formed within the undersurface of the joystick control 40. The recess 54 is defined by a generally continuously-curved surface that provides for a pair of opposed, inwardly-extending shoulders 56 which are positioned in close proximity to the free end 57 of the contact arm 50. A power source 58 such as a battery or AC line current that is transformed and stepped-down to a suitable DC voltage is coupled between the conductors 34 and the variable resistor 52 to complete the electrical circuit. Displacement of the joystick 40 toward either of the extreme positions depicted in phantom in FIG. 1 effects closing of the corresponding switch 44a or 44b and displacement of the contact arm 50 in a manner proportional to that of the joystick in order to effect delivery of an electric current along the respective one of the conductor wires 34 to the resistance heater 32 of the selected directional reorienting device 31.

In the preferred embodiment of the invention, the layers 33 of the reorienting devices 31 are formed from a material having a coefficient of thermal expansion that is at least approximately two, and preferably up to ten or more, times greater than the coefficient for that of the material comprising the catheter tube 26. In the preferred embodiment of the catheter device 20, the layers 33 of the reorienting devices 31 are formed from a suitable silicone rubber and the catheter tube is formed from a suitable one of the family of PTFE compounds. Such an arrangement provides for a disparity in respective coefficients of thermal expansion of on the order of twelve, whereby silicone rubber is characterized by a coefficient of on the order of $670 \times 10^{-6}$ in/in/°F. and the PTFE fluorocarbons are characterized by a coefficient of on the order of $55 \times 10^{-6}$ in/in/°F.

While the foregoing materials have been selected for, among other reasons, their disparity in coefficients of thermal expansion, other factors relating to the environment in which the device is to be used may also necessitate consideration. For example, in instances where the device is to be exposed to body tissues and fluids of a mammalian patient, considerations of optimal device performance, as is obtained from the use of materials exhibiting widely disparate coefficients of thermal expansion, and the extent to which the material is non-antigenic to mammalian tissues and fluids, are of critical importance. It can be readily appreciated that in instances where a risk of adverse antigenic reaction is posed by the use of a plastic material having an extremely favorable coefficient of thermal expansion (i.e., a coefficient that is extremely high or extremely low), prudence would dictate the use of another, albeit less thermally, advantageous material. In a corresponding fashion, in instances where the environment does not dictate such considerations, materials can be selected which provide for more optimal thermal performance.

With further reference to FIG. 2, shown is the preferred heater wire configuration for mounting the heater wire 32 within the layer 33. The heater wire 32 is preferably configured with a generally sinusoidal form comprised of a plurality of laterally outwardly-extending and inwardly-extending undulations 64 and 66 so as to increase the surface area for contact of the wire 32 with the thermally responsive material comprising the reorienting layers 33. The arrangement of undulations, 64 and 66 permits the heater wire 32 to be configured sb as to form two heater wire segments 32a and 32b that are positioned adjacent one another and connected by a common bend 68. Configuration of the heater wire 32 in this manner permits an increase in heater wire surface area from that which would be provided by the use of straight wire segments so as to increase the amount of thermal energy that can be transferred to the material comprising the reorienting layer 33. Thermal energy transfer is further facilitated by configuring the heater wire as a generally flat-sided ribbon of generally polyhedral configuration, as opposed to a circular or oval configuration. Other heater wire configurations, such as those involving multiple layering of the wire within the reorienting layer 33, can be provided in accordance with the present invention.

It is further envisioned as an aspect of the present invention that the thermal energy responsive device 20 can be formed as, an integral, self-contained unit comprised substantially entirely, if not exclusively, of two plastic materials of widely disparate coefficients of thermal expansion. For such arrangements of the present invention, sources of thermal energy such as heater wires 32 embedded in the reorienting layers 33 are not required. This aspect of the invention would have particular utility for use as an implantable or embeddable object where it is desirable to obtain some degree of progressive control arising from deformation of the device 22 upon exposure to thermal energy received thereby from the surrounding environment rather than an embedded heater wire. Such arrangements would have particular applicability for use as implantable devices in mammalian body structures as well as in nonmedical applications, such as for use in progressively responsive thermal switchgear.

Figure 3A:
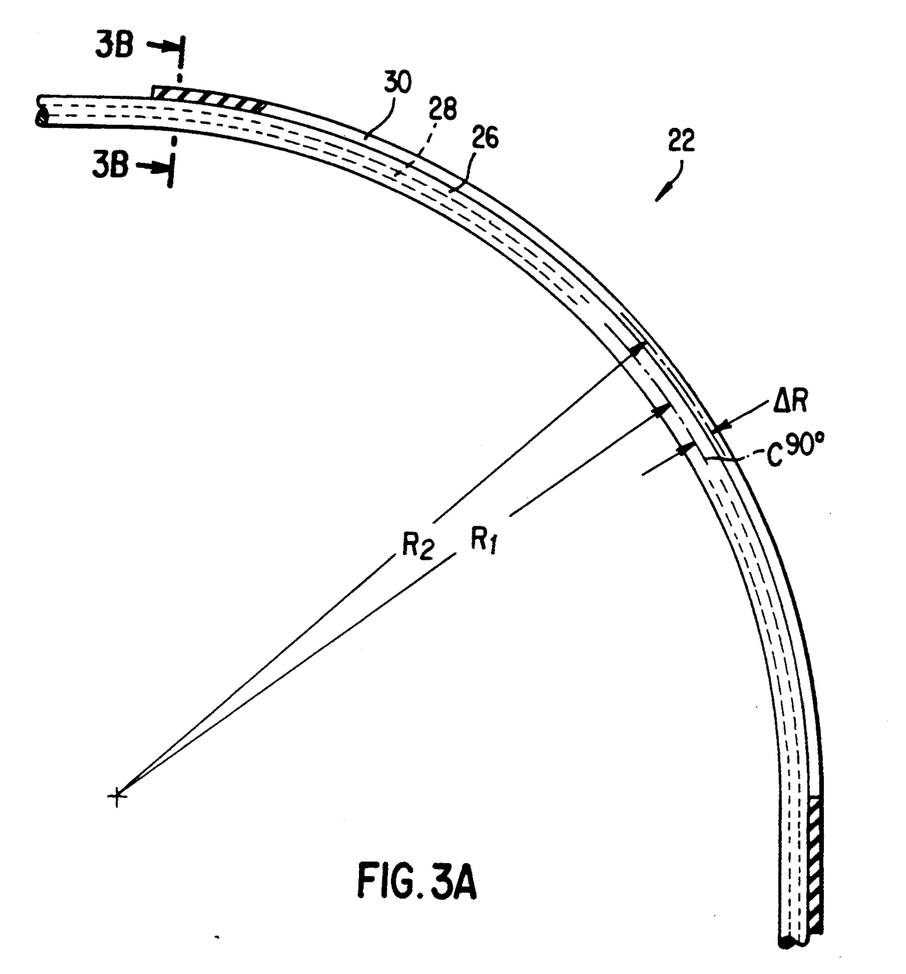
FIGS. 3A and 3B provide an illustrative example of the bending of a catheter through 90° in accordance with the present invention.
Figure 3B:
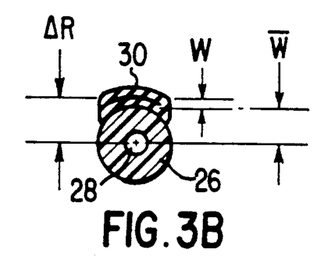

A practical application of the bi-plastic thermal energy responsive device 20 of FIG. 1 is illustrated in FIGS. 3A and 3B. These drawings graphically illustrate the dimensions that may be used to calculate the necessary increase in temperature for effecting bending or turning of a 0.024 inch (0.61 mm) diameter PTFE tubular structure such as a catheter 26 through 90° with a 0.5 inch (1.27 cm) radius. With reference to the drawings, the following relationship is applicable for determining the circumference or length of the catheter tube 26 along a 90° bend:

$$C^{90°} = \frac{2\pi R_1}{4} \quad (1)$$

where $C^{90°}$ is the circumference of the catheter tube 26 about a 90° bend (i.e., the circumference of a quarter circle) and $R_1$ is the radius of curvature of the bend of the catheter tube 26 (Both the circumference $C^{90°}$ and radius $R_1$, are measured with respect to the central longitudinal axis of the catheter tube 26.)

Accordingly, a change in the circumference of the tube 26 is represented by the following relationship:

$$\Delta C^{90°} = \frac{\pi \Delta R}{2} \quad (2)$$

where, $\Delta C^{90°}$ is the change in circumference and $\Delta R$ is the change in the radius of curvature. Such a change in circumference may be as a result of thermal energy input to the device 22 either through a heater wire or from the surrounding environment.

The change in radius of curvature $\Delta R$ for the tube 26 may be determined by the following relationship:

$$\Delta R = R_2 - R_1 = W + w \quad (3)$$

where $R_2$ is the radius of curvature of the directional reorienting device 31 as measured to one-half of the thickness of the device, $w$ is one-half the thickness of the directional reorienting device 31, and $W$ is one-half the thickness of the catheter tube 26. Given the following dimensions:

$W = 0.012$ inch
$w = 0.006$ inch
$R_1 = 0.500$ inch
$R_2 = 0.518$ inch
$\Delta R = 0.018$ inch and solving equation (2) above, $$\Delta C^{90°} \text{ (in)} = \frac{\pi (0.018)}{2} \approx 0.028 \text{ inch.} \quad (4)$$

Based on the above calculation, bending of the device 22 through 90° with a 0.5 inch radius results in a circumference change of approximately 0.028 in (0.71 mm). The amount of thermal energy necessary to be inputted to the device 22 in order to effect the bend, expressed in the form of a temperature increase ($\Delta T$) in °F., is obtained from the following relationship:

$$\Delta T = \frac{\Delta C^{90°} \cdot 2\pi \cdot \Delta R}{4(|Co_1 - Co_2|)} \quad (5)$$

where, $Co_1$ and $Co_2$ represent the coefficients of thermal expansion of the materials of the catheter tube 26 and the directional reorienting device 31, respectively, and $2\pi\Delta R/4$ represents the measurement of a 90° (i.e., one quarter) portion of a circle. For a device 22 as described above formed from silicone rubber ($Co_1$) and PTFE fluorocarbons ($Co_2$), $Co_1 = 670 \cdot 10^{-6}$ in/in/°F. and $Co_2 55/10^{-6}$ in/in/°F. Therefore, $$|Co_1 - Co_2| = 615 \cdot 10^{-6} \text{ in/in/°F.} \quad (6)$$

Substituting equations (4) and (6) into equation (5), $$\Delta T \approx 58° \text{ F.}$$

Therefore, an increase of about 58° F. (14.5° C.) is required to be imparted to the device 22 along the length of the tubular member 24 thereof in order to achieve a 90° bend of the tube along a 0.5 in radius.

The foregoing illustration clearly demonstrates that configuration of the catheter tube 26 as a bi-plastic member in accordance with the teachings of the present invention provides the catheter user with a degree of catheter control that is unprecedented in the medical field. The extent of angular deviation or bending of the catheter tube is directly proportional to the amount of thermal energy imparted to the directional reorienting devices 31. Operability of the catheter device 20 described above is to be clearly contrasted with catheters formed from shape memory metal alloys, where virtually no change in catheter configuration is attained until a predetermined elevated catheter temperature has been reached. Once such a predetermined temperature has been reached, the shape memory material reverts to its pre-shaped form and, unlike the catheter device of the present invention, is not readily controllable between its two extremes of configuration. As a result, catheters formed from shape memory alloys cannot readily be used in blood vessels having angular deviations more extreme than that for which the shape memory material has been preconditioned. This limitation in the prior art is to be contrasted with the catheter device of the present invention which, by virtue of its temperature proportional manner of response, can be used in any of a wide variety of blood vessel configurations.

With reference to FIG. 4A, the arrangement for mounting of the tube directional reorienting devices 31 to the catheter tube 26 is shown. The four directional reorienting devices 31 are arranged into two pairs so as to provide for directional control of the catheter tube 26 relative to two mutually perpendicular axes. In the drawings, the relative dimensions of the directional reorienting devices 31 and the catheter tube 26 have been exaggerated for the sake of clarity.

In the mounting arrangement depicted in FIG. 4A, the directional reorienting devices 31 are positioned along the outer periphery of the tube 26. As the compounds comprising the family of PTFE fluorocarbons exhibit very smooth and uniform surface characteristics when formed into three dimensional objects, it is desirable to alter these characteristics at the sites where the directional reorienting devices 31 are to be positioned therealong in order to facilitate binding of these components to one another. A preferred form of tube surface modification provides for the formation of a plurality of channels or grooves 72. The grooves 72 can be formed in any of a variety of conventional processes, such as by cutting with any of a variety of surface cutters, and can be provided so as to extend generally parallel and/or transverse to the longitudinal axis of the tube 26. Each groove is flanked by a ridge 74, and the grooves and ridges cooperate with one another to provide for a region of surface discontinuity which facilitates bonding of the material comprising the directional reorienting means 30 to the tube 26.

While the devices 31 have been depicted as being positioned along or in communication with an exterior surface of the tube 26, further alternative arrangements, such as those providing for the layers along the walls defining the tubular lumina 28 are contemplated by the present invention. With reference to an alternate embodiment depicted in FIG. 4B, the directional reorienting devices 31' may be received within correspondingly-dimensioned channels 70 formed within the periphery of the catheter tube 26. The channels 70 can be provided with a variety of cross-sectional configurations, such as that depicted in the drawing in which the channel sidewalls 70a and 70b converge toward one another as they extend from a common base wall 70c. The exterior surface 71 of the directional reorienting device 31' is preferably provided with a gently curved configuration which, when combined with the multi-channeled configuration of the tube 26, provides for a generally annular cross-sectional tube configuration which facilitates insertion and passage of the catheter into a blood vessel.

Figure 5:
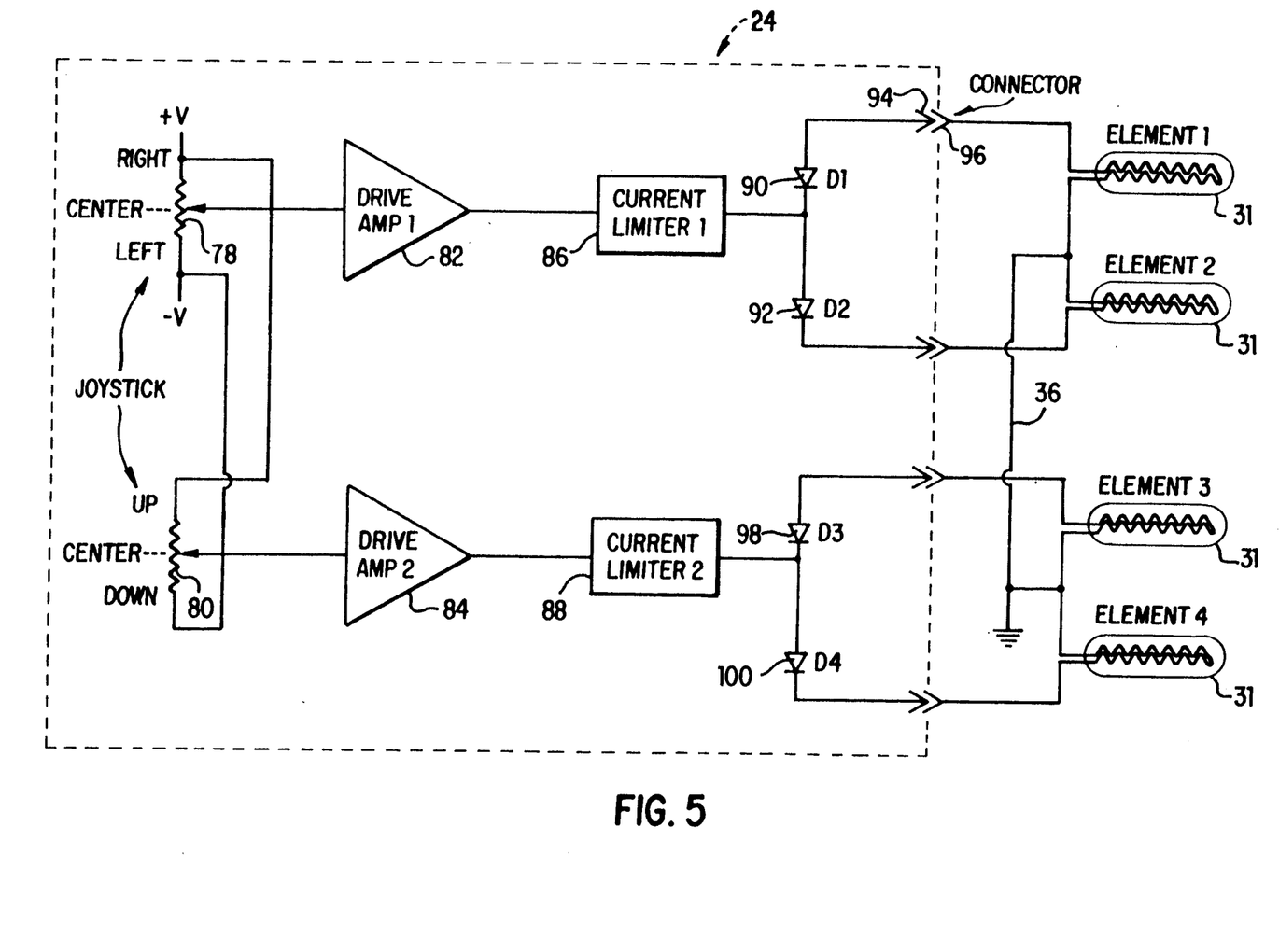
FIG. 5 is a schematic illustration of an electrical control arrangement for implementing directional control of the device of FIG. 1.

FIG. 5 illustrates in schematic form the control arrangement for implementing directional control of a device 20 that is configured in the manner depicted in FIGS. 4A and 4B to be controllable along at least two mutually perpendicular axes. The control device 24 is denoted by the phantom line in the drawing. The depicted arrangement is applicable for use with a joystick controller, key pad controller, rotary controller, or any of a variety of other control input devices. The control unit 24 preferably comprises first and second variable resistors 78, 80, each of which is connected to a corresponding drive amplifier 82, 84. As can be appreciated by persons of ordinary skill in the art, the resistance exhibited by each of the variable resistors 78, 80 varies in accordance with the position of the control input device (i.e., joystick, etc.) so as to vary the amount of current passed through the corresponding current limiter 86, 88 for passage ultimately to the corresponding one or more of the directional reorienting devices 31.

With reference to control of the directional reorienting devices 31 corresponding to elements 1 and 2, output from current limiter 86 is directed to either of the diodes 90, 92 in accordance with the voltage polarity that is applied across the resistor 78. Current passing through the respective one of the diodes 90, 92 is conducted to a connector receptacle 94 for passage to the appropriate one of the directional reorienting devices 31 corresponding to elements 1 and 2 through a suitable connector 96 and an associated conductor wire 34 extending therefrom. The flow of current from the second variable resistor 80 to the corresponding directional reorienting devices 31 corresponding to elements 3 and 4 proceeds in a manner analogous to that described above, with current output from the current limiter 88 being directed to an appropriate one of the diodes 98, 100 in accordance with the voltage polarity that is applied across the variable resistor 80.

It will be appreciated from the foregoing description that user movement of the joystick or other directional control input device is translated into an appropriate voltage across one or both of the variable resistors 78, 80 to provide for the delivery of a current to effect resistance heating of the heater wire 32 embedded in the respective one or more of the directional reorienting devices 31, which in turn effects bending of the catheter tube 26 to a predetermined extent in a predetermined direction. As directional input can be imparted to the devices 31 for varying degrees of movement along the respective mutually perpendicular axes, bending of the tube 26 in a wide range of angular directions between the respective axes can be attained. For example, equal input to the resistors 78 and 80 will result in bending of the tube 26 in a direction which extends 45° between the mutually perpendicular axes, whereas unequal input will result in tube bending from 0° to 90° with respect to the respective axes of control.

Figure 6A:
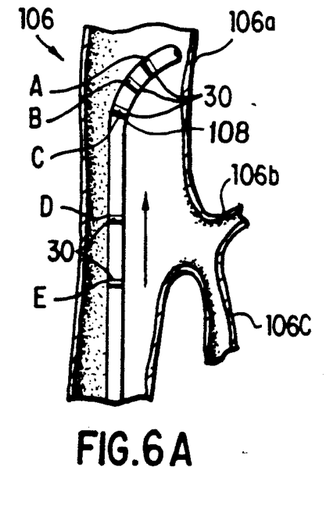
FIGS. 6A–6C are schematic views illustrating a series of steps for controlling the directing of a catheter device in accordance with the present invention through a vascular structure.
Figure 6B:
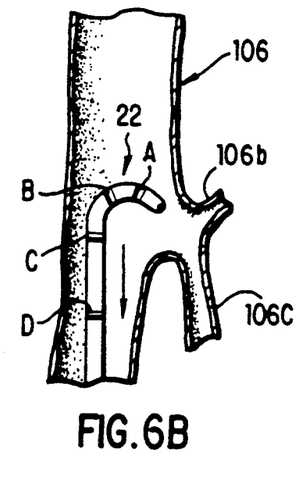
Figure 6C:
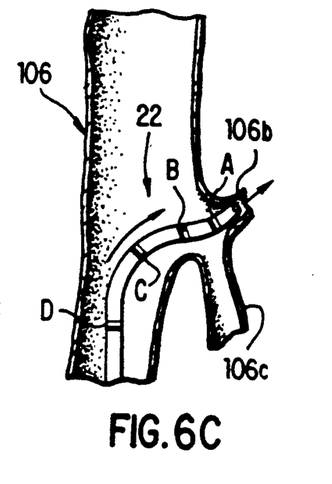

Advancement of the catheter 22 formed in the manner described hereinabove through an anatomical site such as a vascular structure 106 is depicted in FIGS. 6A-6C. Vascular structures similar to that depicted in FIGS. 6A-6C can be found, for example, in the celiac axis in the vicinity of the common hepatic and splenic arteries. The dimensions of the catheter 22 with respect to the blood vessel 106 have been exaggerated for the sake of clarity. The depicted catheter includes five discrete zones A-E, each of which is provided with a direction reorienting assembly 30. The direction reorienting assemblies 30 are preferably arranged to permit independent directional control of each zone so as to provide the user with a precise degree of catheter control as the various zones of the catheter are advanced through the anatomical structure 106. A visualization marker 108 can be provided adjacent each of the zones A-E to assist the user in visualizing the position of each respective zone as it is advanced through the blood vessel 106. The markers 108 can be formed from gold or any other suitable material that renders the marker visible during the course of the catheterization procedure. Gold is preferred for the marker material when the catheter is to be used in a radiographic catheter imaging process due to this element's radio-opacity to x-ray radiation and its relative non-reactivity with mammalian tissue and fluids.

With continuing reference to the drawings, the vascular structure 106 comprises a primary vessel segment 106a and branching segments therefrom 106b and 106c. In order to traverse the curvilinear path extending from vessel segment 106a through 106b, the catheter is advanced (FIG. 6A) in the direction of the arrow beyond the branched segments 106b and 106c, and thermal energy is directed in the manner described above to the directional reorienting devices for zones A and B in order to effect bending of the catheter tube 22 toward the blood vessel branch 106b. Following bending of the tube adjacent the respective zones to the desired extent, the tube 22 is retracted (FIG. 6B) toward the entry site to the vessel 106b so as to traverse the bend extending therebetween. Once the bend has been traversed, thermal energy is imparted in the manner described above to each of the zones A and B so as to generally straighten the section of catheter adjacent to these respective zones. At about the same time, energy is imparted to zone C so as to effect bending of the tube at this zone toward the vessel branch 106b (FIG. 6C) in order to facilitate advancement of the catheter tube 22 into and through the vessel branch 106b. Thermal energy is imparted to zones D and E in a fashion similar to that described above with reference to zone C so as to further facilitate advancement of the portion of the tube adjacent these respective zones into the vessel branch 106b. It will be appreciated that the number and placement of zones along the length of the catheter tube can vary in accordance with such factors as, for example, the anatomy of the structure to be catheterized, the dimensions and flexibility of the catheter tube, and user preference.

With reference to FIGS. 7-10, there are depicted details of an alternative arrangement for a thermal energy responsive device, designated generally by reference character 201, in which optical energy rather than electrical energy is utilized to provide the desired elevation in temperature of the directional reorienting assemblies 30' incident to effecting bending of the tube 26' to the desired extent and direction. This optical energy embodiment can be advantageous for use in environments where the passage of electrical currents along the length of the tube 26' and associated field effects are to be avoided.

The materials respectively co sing the tube 26' and direction reorienting layers 31' of the optical energy aspect of the invention can be the same as those described above with reference to FIGS. 1-5. The directional reorienting assemblies 301 as shown are positioned along the outer surface of the tube 26' so as to form three discrete zones, designated A' through C'. Both the number and placement of zones can vary for the same reason noted above with respect to the aspect of the invention depicted in FIGS. 1-5. The respective reorienting devices 31' comprising each of the assemblies 301 are arranged in a manner analogous to that depicted in FIG. 4A so as to provide for bending of the tube 26 along at least two mutually perpendicular axes. As with the arrangement depicted in FIGS. 1-5, it is to be appreciated that a greater or lesser number of directional reorienting devices 31' can be provided at each zone so as to provide for bending of the tube with respect to a desired arrangement and number of axes.

Figure 7:
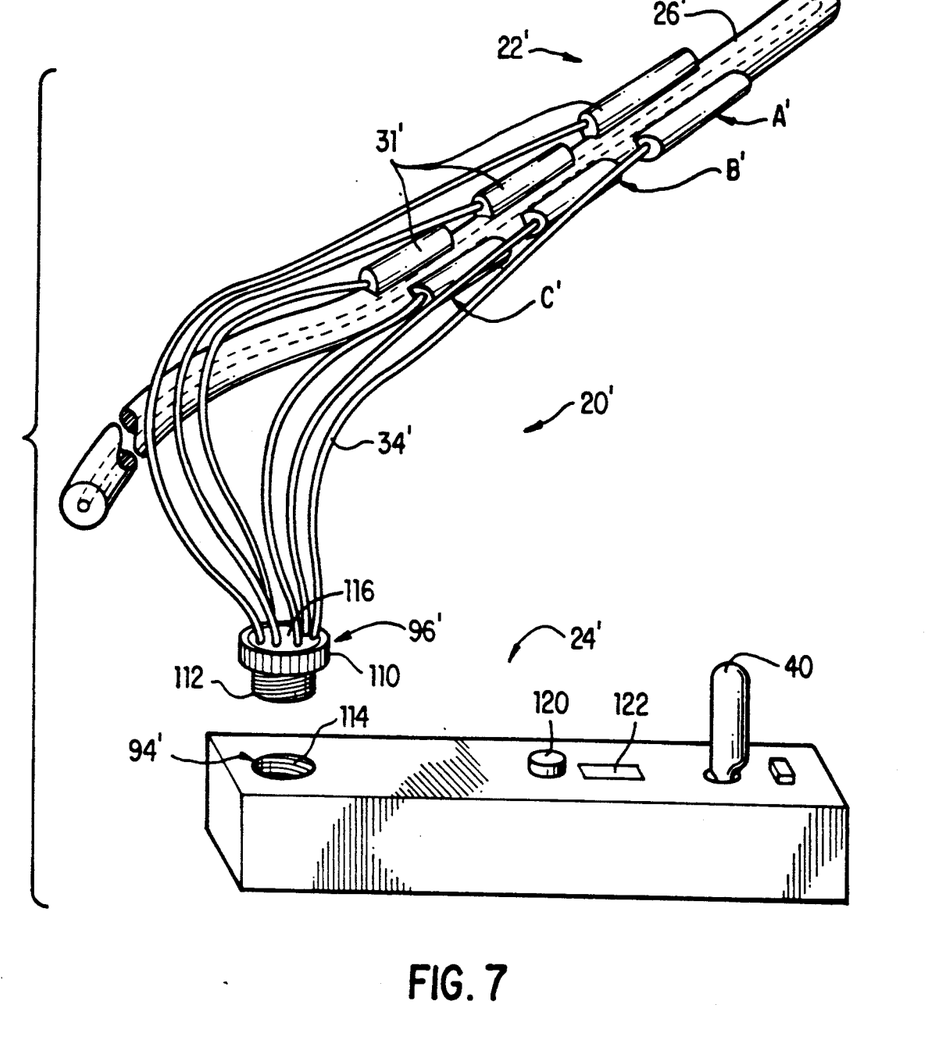
FIG. 7 illustrates a perspective view of an alternative embodiment of the invention employing optical energy.

Optical energy is delivered to the directional reorienting devices 31' through fiber optic leads 34'. Each of the leads can be provided with a metallic coating to facilitate internal reflection and can be provided with a darkened exterior surface to promote energy absorption from the surrounding use environment. In the preferred embodiment, a single fiber optic lead 34' extends to each of the directional reorienting devices 31'. However, other arrangements, such as those involving coupling of a single fiber optic lead to the directional reorienting devices 31' of each assembly 30', can be provided. Each of the leads 34' terminates at its proximal end at a connector 96' which is adapted to be received within a connector receptacle 94' associated with the control device 24'.

While the connector 96' and corresponding connector receptacle 94' can have any of a wide variety of conventional complementary designs, use of a threaded connector can be advantageous for providing positive engagement between the connector 96' and receptacle 94'. With reference to FIG. 7, the connector 96' includes an externally threaded collar 110 having threads 112 that are configured and dimensioned to engage complementary threads 114 provided along the surface of the connector receptacle 94'. The collar 110 defines a central aperture which receives a base 116 through which the proximal ends of each of the fiber optic leads 34' are received for optical coupling in a conventional manner with appropriate optical energy output devices (not shown) associated with the control device 24'. Preferably, the collar 110 and base 116 are displaceably mounted relative to one another so as to inhibit binding or twisting of the leads 34' extending from the receptacle.

The control device 24' includes a directional input device such as a joystick 40 that is configured in an analogous manner to that described above in connection with the embodiment of the device depicted in FIGS. 1-5 for controlling energy output from the control 24' to the catheter 22'. In this aspect of the invention, optical energy is provided: in the manner described below by a suitable source of optical energy such as a GaAlAs laser diode or tunable laser. When the control 24' includes a tunable laser, appropriate wavelength selector means 120 and associated wavelength display means 122 can be provided. While the selection of wavelength can vary in accordance with the composition of the material to be heated, energy having a wavelength from about 700 nm to about 900 nm is preferred for supplying optical energy to directional reorienting means 30' formed from silicone rubber.

Figure 8:
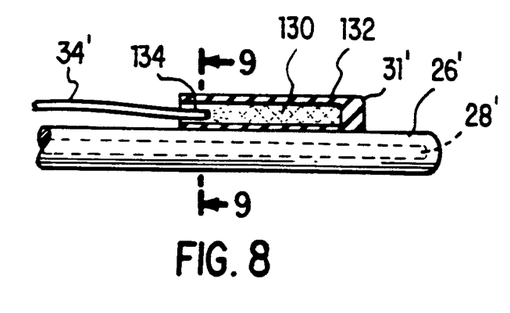
FIG. 8 is a partial sectional side view of a portion of the device depicted in FIG. 7.
Figure 9:
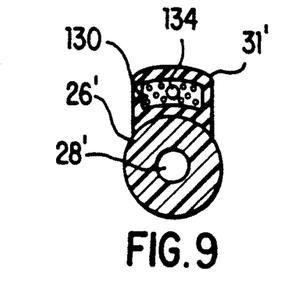
FIG. 9 is a sectional view taken along the line 9—9 of FIG. 8.

With reference to FIGS. 8 and 9, there is depicted the preferred configuration for the directional reorienting devices 31' for use in conjunction with the receipt of optical energy. While each block constituting the devices 31' can be provided with a substantially uniform and solid cross-sectional configuration, it is preferred that the block 31' define an open chamber 130 which extends substantially parallel to the principal axis of the block to allow for a substantially even distribution of optical energy for radiation to the material comprising the block 31'. The block surface 132 defining the chamber 130 is preferably provided with a smooth, uniform surface to facilitate internal reflection of the optical energy within the chamber. The distal end 134 of the fiber optic lead 34' is embedded in the block 31' in such a fashion so as to preferably extend partially into the chamber 130. It is to be understood, however, that other mounting arrangements for securing the lead distal end 134 within the block 31' can be provided. Furthermore, it is to be appreciated that, while a single lead 34' is depicted as extending to each of the blocks 31', the depicted single lead can instead be in the form of a cable comprising a plurality of discrete fiber optic leads for conveying optical energy to the blocks 31'. Optical energy transmitted to the blocks 30' in any of the foregoing ways is radiated to the material comprising the block to cause an elevation in block material temperature to effect its elongation and, therefore, angular deviation or bending of the portion of the tube 26' to the desired extent and direction.

Figure 10:
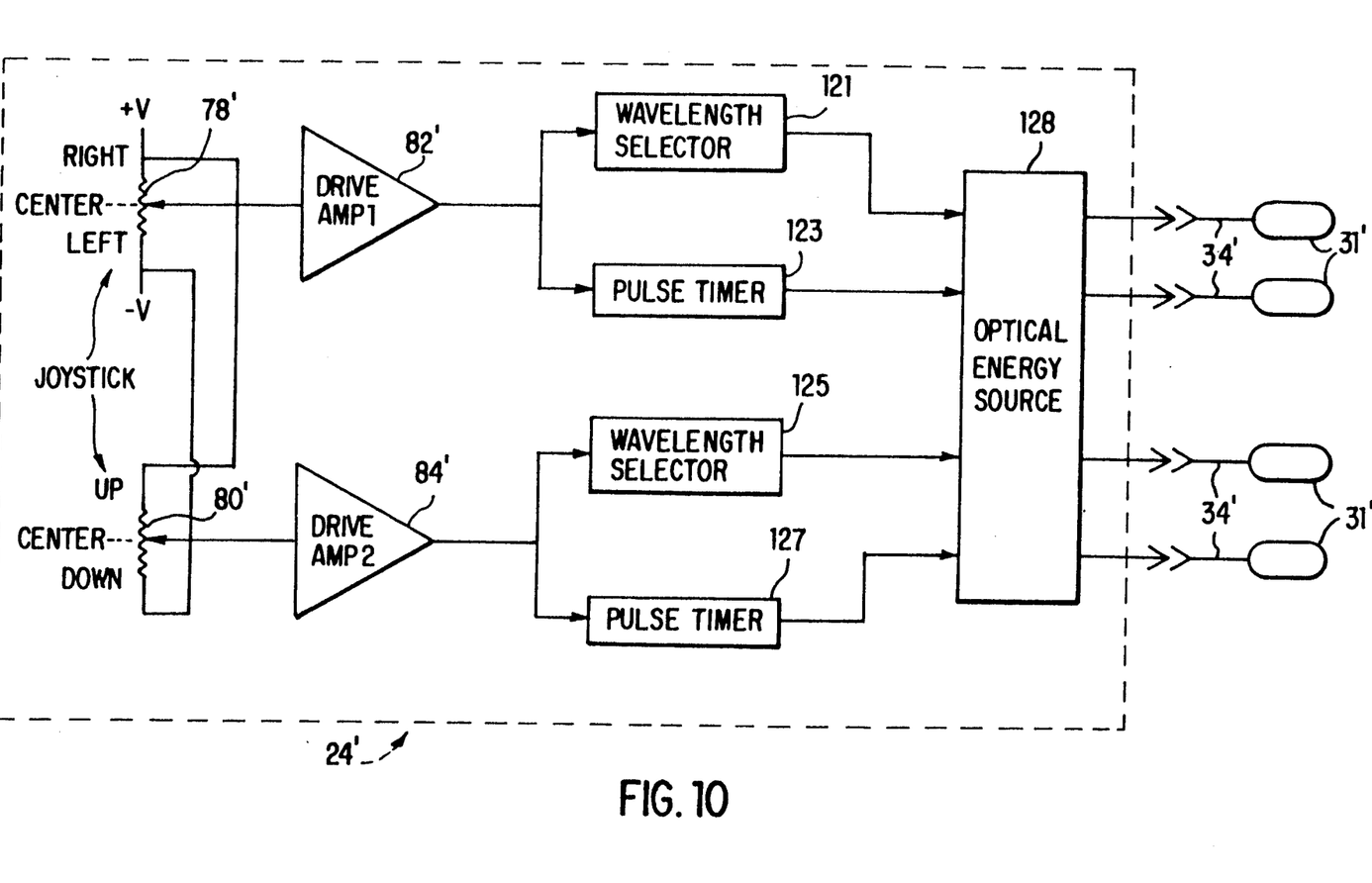
FIG. 10 is a schematic illustration of an optical control arrangement for implementing control of the device of FIG. 7.

FIG. 10 illustrates in schematic form the circuitry that is associated with implementing optical energy input to the directional reorienting devices 31'. The figure provides a schematic circuit diagram for a single-zone, two-axis range of directional control and operates in a manner generally analogous to that described above in connection with FIG. 5. In particular, first and second variable resistors 78', 80' are provided to vary the signal input to associated drive amplifiers 82', 84' in accordance with joystick position. As was the case with the arrangement depicted in FIG. 5, signal input for controlling directional input for movement along one axis is depicted in the upper half of the drawing, whereas signal input for controlling directional input along a second axis which is perpendicular to the first axis is depicted in the lower portion of the drawing. As noted above, control for a different orientation or number of axes of movement can be provided in accordance with the present invention. Output from the respective drive amplifiers 82', 84' is directed in parallel to a corresponding wavelength selector and pulse time-pair, labelled 121, 123 and 125, 127 in the drawings, for processing and routing of signal input to appropriate directional reorienting devices 31' that have been provided for controlling movement of the catheter tube 26' along the associated one or more axes of movement. An optical energy pulse is generated by optical energy source 128 in accordance with signal input parameters from the wavelength selector and pulse timer pairs that is commensurate to the quantum of energy that is required to accomplish the desired extent of deviation along the respective axis of movement that is inputted to the control 24' through the joystick 40. As noted previously, the optical energy source 128 is preferably in the form of a laser diode or tunable laser which is capable of generating optical energy output of an appropriate wavelength and pulse duration to the selected directional reorienting devices 31' through the fiber optic leads 34' in the manner described above.

The foregoing detailed description is illustrative of various embodiments of the thermal energy responsive device of the subject invention. It will be appreciated from the foregoing description that variations can be made to the invention as set forth hereinabove and in the accompanying drawings, and such variations are expressly intended to be encompassed by this description and the accompanying claims.

What is claimed is:

1. A thermal energy responsive surgical device insertable into the body of a patient, the device comprising:
    a generally cylindrical flexible member comprising a first non-metallic material having a coefficient of thermal expansion;
    at least one strip formed from a second non-metallic material, said strip being bonded to said flexible member, said second non-metallic material having a coefficient of thermal expansion greater than that of said first non-metallic material; and
    a supply system for supplying thermal energy to said second non-metallic material strip from a position remote therefrom to effect expansion of said second non-metallic material strip and a change in angular configuration of said flexible member.

2. The device according to claim 1, wherein said thermal energy supply system comprising a resistance heater wire connected to said strip and a source of electrical energy.

3. The device according to claim 2, wherein said heater wire is comprised of a nickel metal alloy.

4. The device according to claim 2, wherein said heater wire is provided with a generally sinusoidal configuration along at least a portion of its length.

5. The device according to claim 1, wherein said thermal energy supply system comprises an optical energy source.

6. The device according to claim 5, wherein said thermal energy supply system comprises at least one optical fiber which extends from said optical energy source to said second material layer.

7. The device according to claim 6, wherein a darkened exterior surface is provided along at least a portion of the length of at least one of said optical fibers.

8. The device according to claim 6, wherein at least two of said second non-metallic material layers are positioned along said flexible member, a plurality of optical fibers being provided and arranged such that at least a single one of said plurality of optical fibers extends from said optical energy source to each of said two second non-metallic material layers.

9. The device according to claim 5, wherein said optical energy source comprises at least one laser energy source.

10. The device according to claim 9, wherein said laser energy source is operable to emit optical energy having a wavelength in the range of from about 700 nm to about 900 nm.

11. The device according to claim 1, wherein said flexible member defines a tubular lumen along at least a portion of its length.

12. The device according in claim 1, wherein said flexible member comprises a radio-opaque indicator adjacent at least one of said non-metallic material layers.

13. The device according to claim 1, wherein said flexible member comprises a plurality of strips formed from said second non-metallic material positioned therealong.

14. The device according to claim 13, wherein said thermal energy supply system is operable to independently deliver thermal energy to at least two of said plurality of strips.

15. The device according to claim 14 wherein at least two of said plurality of second material strips are positioned laterally adjacent one another at a common level along said flexible member.

16. The device according to claim 15 wherein at least three second material a strips are provided along said flexible member at said common level thereof, at least two of said second material strips positioned at said common level being independently controllable by said thermal energy supply system.

17. The device according to claim 13, wherein said plurality of strips are arranged to form at least two zones located at different longitudinal positions along the flexible member.

18. The device according to claim 17 wherein the strips comprising two of said zones are controllable independently from one another.

19. The device according to claim 1, wherein said first non-metallic material comprises a polymerized halogenated hydrocarbon.

20. The device according to claim 19, wherein said polymerized halogenated hydrocarbon comprises a polyfluorinated alkylene.

21. The device according to claim 1, wherein said second non-metallic material comprises a silicone rubber.

22. The device according to claim 1, wherein said second material is received within at least one groove formed within said first material layer.

23. The device according to claim 1, further comprising an expansion control system for progressively controlling expansion of said strips of second material.

24. The device according to claim 1, wherein the material comprising said second material exhibits a coefficient of thermal expansion at least twice that of the material comprising said first material layer.

25. The device according to claim 1, wherein at least one of said first and second materials is comprised of a material that is non-antigenic to mammalian tissue.

26. An energy-responsive bi-plastic switch, comprising:
   a first member formed from a first plastic material having a coefficient of thermal expansion; and
   a second member positioned along at least a portion of said first member and being formed from a second plastic material having a coefficient of thermal expansion greater than that of said first plastic material, said second member being responsive to thermal energy input to effect a change in angular orientation of the adjacent portion of the first member.

27. The bi-plastic switch according to claim 26, further comprising a supply system for supplying thermal energy to said second material member to effect expansion thereof.

28. The bi-plastic switch according to claim 27, wherein said thermal energy supply system comprises a resistance heater wire coupled to said second material member.

29. The bi-plastic switch according to claim 27, wherein said thermal energy supply system comprises an optical energy source.

30. The bi-plastic switch according to claim 29, wherein at least one optical fiber is provided to transmit said optical energy from said optical energy source to said second material member.

31. The bi-plastic switch according to claim 26 wherein at least two zones of second material members are provided along a surface of said first material layer at different longitudinal positions thereof.

32. The bi-plastic switch according to claim 31, further comprising a control system for independently supplying said thermal energy to each of said zones.

33. The bi-plastic switch according to claim 32, wherein said control system is operable to modulate the amount of thermal energy to be supplied to said second material member comprising at least one of said zones.

34. The bi-plastic switch according to claim 23, wherein the amount of thermal energy supplied to said second material member is modulated by varying electrical current flow to said second material layer.

35. The bi-plastic switch according to claim 32, wherein the amount of thermal energy supplied to said second material member is modulated by varying at least one of the duration and rate of optical energy pulse generation of pulses conveyed to said second material member.

36. The bi-plastic switch according to claim 26, wherein said first material member comprises a polymerized halogenated hydrocarbon.

37. The bi-plastic switch according to claim 36, wherein said polymerized halogenated hydrocarbon comprises a polyfluorinated alkylene.

38. The bi-plastic switch according to claim 26, wherein said second material member comprises a silicone rubber.

39. The bi-plastic switch according to claim 38, wherein said first material member comprises a material having a coefficient of thermal expansion that is up to about 20% as high as that of said silicone rubber.

40. The bi-plastic switch according to claim 26 wherein said first and said second material members are comprised of materials that are non-antigenic to mammalian tissue.

41. The bi-plastic switch according to claim 26, wherein said first material layer is configured as a generally cylindrical tubular member which defines a tubular lumen that extends along at least a portion of the length of the tubular member.

42. The bi-plastic switch according to claim 41, wherein said second material member is positioned along an exterior surface of said tubular member.

43. A method for effecting bending of a first member in response to thermal energy input to a second member positioned adjacent the first member, comprising the steps of:
   forming the first member from a non-metallic flexible material having a relatively low coefficient of thermal expansion;
   forming the second member from a non-metallic flexible material having a coefficient of thermal expansion that is at least twice that of said first non-metallic material;
   bonding the second member along at least a portion of the first member; and
   receiving thermal energy with said second member to effect expansion thereof and bending of the first member in a predetermined direction generally away from said second member.

44. The method according to claim 43 wherein said second member is secured to said first member by receiving at least a portion of the second member within at least one groove formed within the first member.

45. The method according to claim 43, wherein said first and second non-metallic materials are selected from the family of compounds that are non-antigenic to mammalian tissue.

46. The method according to claim 43, wherein said first member is formed from a polytetrafluoroethylene.

47. The method according to claim 43, wherein said second member is formed from a silicone rubber.

48. The method according to claim 43, wherein said thermal energy arises from the delivery of electrical energy to a metallic member associated with said second member.

49. The method according to claim 43, wherein said thermal energy arises from the delivery of optical energy to said second member.

50. The method according to claim 49 wherein said optical energy is in the form of electromagnetic energy having a wavelength of from about 700 nm to about 900 nm.

51. The method according to claim 49, wherein said optical energy is passed through at least one optical fiber to said second member.

52. The method according to claim 51, wherein said optical fiber is provided with a darkened exterior surface along at least a portion of its length.

53. The method according to claim 51, wherein said optical fiber is provided with a metallic coating along at least a portion of its length.

54. An energy responsive device operable to change directional orientation along at least a single axis, comprising:
   an elongated flexible member comprising a first non-metallic material having a coefficient of thermal expansion;
   a plurality of strips coupled to said flexible member, said strips being formed from a second, non-metallic material and arranged its discrete zones along said flexible member, said zones being longitudinally spaced apart from one another along the length of said flexible member; and an energy supply system for imparting thermal energy to a predetermined one or more strip in at least one of said zones from a position remote therefrom to effect expansion of said one or more strips and a change in angular orientation of said flexible member.

55. The device according to claim 54, wherein said energy supply system comprises a resistance heater wire connected to at least one of said strips and an electrical energy source connected to the wire.

56. The device according to claim 54, wherein said energy supply system comprises an optical fiber connected to at least one of said strips and a source of optical energy connected to the fiber.

57. The device according to claim 54, further comprising a control system connected to said energy supply system that is operable to direct said energy to at least one of said zones.

* * * * *